(12) United States Patent
Felici et al.

(10) Patent No.: US 8,791,437 B2
(45) Date of Patent: Jul. 29, 2014

(54) DEVICE FOR SHAPING AN ELECTRON BEAM OF A MACHINE FOR INTRAOPERATIVE RADIATION THERAPY

(75) Inventors: Giuseppe Felici, Vicenza (IT); Alessia Ciccotelli, Vicenza (IT); Vincenzo Iacoboni, Vicenza (IT); Fabio De Angelis, Vicenza (IT); Nicola Mangiaracina, Vicenza (IT); Aquilino Gava, Vicenza (IT)

(73) Assignee: S.I.T.—Sordina IORT Technologies S.p.A., Vicenza (VI) (IT)

( * ) Notice: Subject to any disclaimer, the term of this patent is extended or adjusted under 35 U.S.C. 154(b) by 0 days.

(21) Appl. No.: 13/879,608

(22) PCT Filed: Oct. 13, 2011

(86) PCT No.: PCT/IT2011/000348
§ 371 (c)(1),
(2), (4) Date: Sep. 25, 2013

(87) PCT Pub. No.: WO2012/049700
PCT Pub. Date: Apr. 19, 2012

(65) Prior Publication Data
US 2014/0054471 A1 Feb. 27, 2014

(30) Foreign Application Priority Data
Oct. 14, 2010 (IT) ................ RM2010A0545

(51) Int. Cl.
*A61N 5/00* (2006.01)
(52) U.S. Cl.
USPC ....... 250/492.3; 250/492.1; 378/65; 378/150; 378/206
(58) Field of Classification Search
USPC ............. 378/65, 150, 206; 250/492.1–492.3
See application file for complete search history.

(56) References Cited

U.S. PATENT DOCUMENTS

| 3,322,950 | A | * | 5/1967 | Bailey et al. ............. 378/65 |
| 4,987,309 | A | | 1/1991 | Klasen |
| 6,703,632 | B1 | | 3/2004 | Macklis |
| 2009/0074148 | A1 | | 3/2009 | Echner |
| 2012/0093293 | A1 | * | 4/2012 | Carol et al. ............. 378/65 |

FOREIGN PATENT DOCUMENTS

FR 2764199 A1 12/1998

OTHER PUBLICATIONS

International Search Report Dated Feb. 2, 2012.

* cited by examiner

*Primary Examiner* — Michael Maskell
(74) *Attorney, Agent, or Firm* — Hedman & Costigan, P.C.; James V. Costigan; Kathleen A. Costigan

(57) ABSTRACT

The present invention concerns a device for shaping an electron beam of a machine for intraoperative radiation therapy (IORT—Intra Operative Radiation Therapy) using a tubular applicator (3) having a duct through which the electron beam is transmitted, the device being characterised in that it comprises a slab (1), provided with a hole (2) corresponding to the duct of the tubular applicator (3), and at least one planar element (10) comprising an upper plate (11) and a lower plate (12) removably attachable to each other through first mechanical coupling means (13), said at least one planar element (10) being removably attachable to the slab (1) through second mechanical coupling means (13, 14) so that the arrangement of said at least one planar element (10) with respect to the slab (1) is adjustable so as to define an aperture (20) of lower area than that of the section of the duct of the tubular applicator (3), the upper plate (11) of each planar element (10) being made of a first sterilisable biocompatible material with a first atomic number, the lower plate (12) of each planar element (10) being made of a second sterilisable biocompatible material with a second atomic number larger than the first atomic number, whereby the lower plate (12) attenuates X-rays produced by the upper plate (11).
The present invention further concerns an automatic method for computing distribution of dose radiated by a IORT machine through such device for shaping an electron beam.

10 Claims, 6 Drawing Sheets

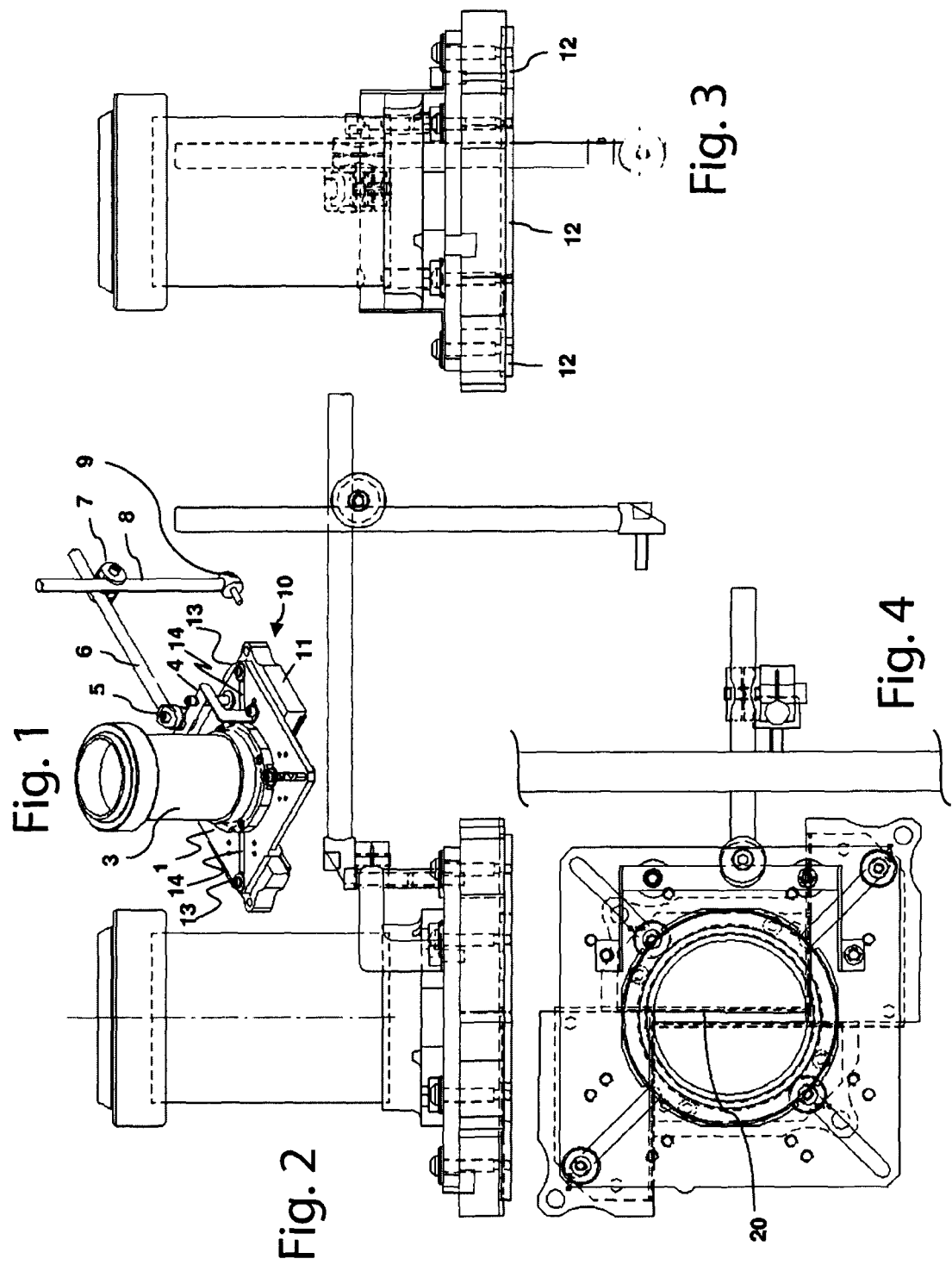

Fig. 7
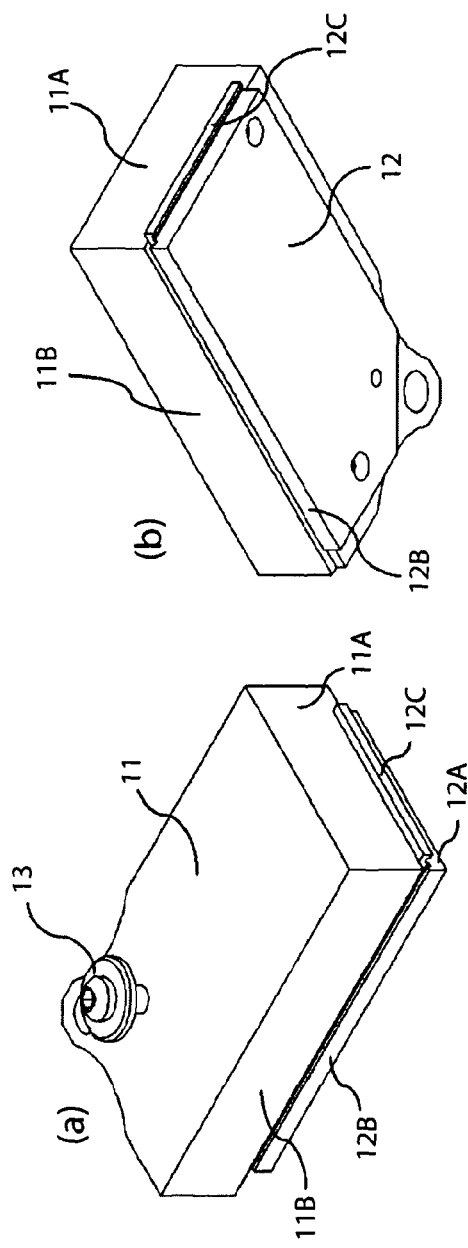
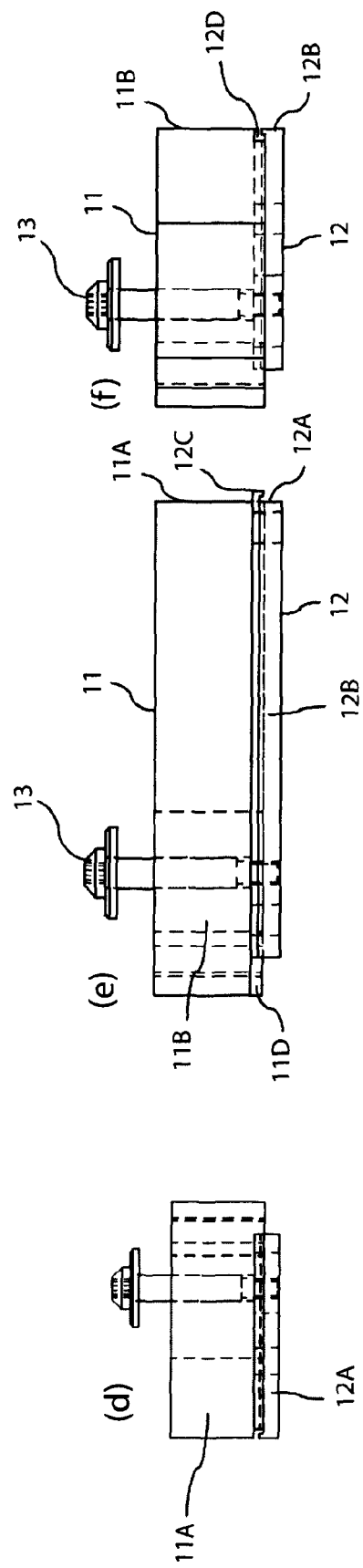

DEVICE FOR SHAPING AN ELECTRON BEAM OF A MACHINE FOR INTRAOPERATIVE RADIATION THERAPY

The present invention relates to a device for shaping an electron beam of a machine for intraoperative radiation therapy (IORT—Intra Operative Radiation Therapy), allowing in a simple, effective, reliable, safe, and inexpensive way, to shape the electron beam generated by a IORT machine ensuring safety of the patient and the environmental radiation protection.

The present invention further relates to a method for computing the electron beam dose radiated on organs and tissues by a IORT machine subjected to radiation after such device and a IORT machine provided with such device.

It is known that intraoperative radiation therapy (IORT) is an innovative technique that is increasingly spreading in the world for treating several neoplasias also thanks to the development of mobile machines. The architecture of machines dedicated to IORT enables radiation of targets having substantially cylindrical or elliptical symmetry: conveyance of the beam on target occurs through circular applicators comprising cylindrical tubes made of metal (as for the Mobetron machine available from InfraOp Medical Corp.) or of polymethylmethacrylate (PMMA) (as for the Novac 7 machine from NRT S.p.A. or for the LIAC machine from Sordina S.p.A.).

In the following of the description reference will be mainly made to the LIAC machine from Sordina S.p.A. However, it must be considered that what will be illustrated is valid for any machine for IORT, and that the device and the method according to the invention are applicable to any machine for IORT, either mobile or stationary, for any energy of the generated electrons, still remaining within the scope of protection of the present invention.

The LIAC available from Sordina S.p.A. company is a mobile accelerator conceived for executing an IORT treatment in operating room. The LIAC comprises a mobile unit, provided with linear accelerator with radiating head, and an operating control rack wired connected to each other. The energy of the generated electrons is adjusted by varying the radiofrequency (RF) power generated by a magnetron; in particular, two versions of LIAC are available, with energies of 4-6-8 and 10 MeV and of 6-8-10 and 12 MeV, respectively.

The radiating unit, having low weight, is extremely movable, facilitating the procedure of preparation of the machine, requiring that the applicator is rigidly attached to the radiating head of the radiating unit (also known as "hard-docking" procedure). In particular, each of the applicators employed with the LIAC comprises a proximal element, that is attached to the radiating head, and a distal element, that is placed in contact with the area to radiate and attached to the proximal element. The PMMA applicators of the LIAC are 60 cm long and 0.5 cm thick, wholly sterilisable and available in various diameters (from 30 to 100 cm) and application angles.

The repetition frequency is varied from 10 to 40 Hz so as to ensure a dose rate larger than or equal to 10 Gy/min with an applicator of diameter equal to 100 mm. In any case, it is possible to obtain larger dose rate, up to 30 Gy/min.

The field obtainable with circular applicator has an obvious cylindrical symmetry, that is perfectly adequate for treatment of different neoplasias, most of all of breast; moreover, in this case the protection of healthy tissues below the volume to radiate is ensured by the use of a radiation protection disc of diameter corresponding to that of the applicator.

The cylindrical symmetry is adequate for IORT treatment of the breast because the radiation target is constructed by the surgeon, as illustrated for instance by U. Veronesi, R. Orecchia in "Intraoperative electrons", *Semin Radiat Oncol.* 2005 Apr; 15(2): pages 76-83.

However, the presently available machines for IORT are inadequate for the treatment of neoplasias which intrinsically have an irregular shape (e.g. long and narrow) not reducible to the circular symmetry (such as for instance in sarcomas), because target geometry is not correctly covered by a circular field without involving in the treatment also healthy tissues and organs at risk. In this regard, it is not possible to radiate a target having an irregular shape by subdividing it into a plurality of circles, because two circles are not joinable with no overlap and, hence, the target would have areas radiated many times which would receive excessive radiation doses or areas less radiated than other with insufficient radiation doses.

It is therefore an object of the present invention to allow in a simple, effective, reliable, safe, and inexpensive way to suitably shape the electron beam generated by a IORT machine in conformity to the clinical target to radiate.

It is still an object of the present invention to allow the computation of the dose of the shaped electron beam that is radiated on organs and tissues subjected to radiation.

It is specific subject matter of this invention a device for shaping an electron beam of a machine for intraoperative radiation therapy (IORT—Intra Operative Radiation Therapy) using a tubular applicator having a duct through which the electron beam is transmitted, the device being characterised in that it comprises a slab, provided with a hole corresponding to the duct of the tubular applicator, and at least one planar element comprising an upper plate and a lower plate removably attachable to each other through first mechanical coupling means, said at least one planar element being removably attachable to the slab through second mechanical coupling means so that the arrangement of said at least one planar element with respect to the slab is adjustable so as to define an aperture of lower area than that of the section of the duct of the tubular applicator, the upper plate of each planar element being made of a first sterilisable biocompatible material with a first atomic number, the lower plate of each planar element being made of a second sterilisable biocompatible material with a second atomic number larger than the first atomic number, whereby the lower plate attenuates X-rays produced by the upper plate.

Always according to the invention, the device may comprise at least two planar elements capable to be arranged so as to be adjacent to each other, each planar element being capable to slide with respect to another adjacent planar element through mechanical guide and slide means, whereby the reciprocal arrangement of said at least two planar elements is adjustable so as to define said aperture.

Still according to the invention, said mechanical guide and slide means may comprise at least one slider and at least one corresponding guide.

Furthermore according to the invention, said planar elements may be four, each planar element having a first side provided with a projecting edge, preferably with L-shaped section, and a second side provided with a notch, preferably with L-shaped section, of shape and size corresponding to the ones of the projecting edge, whereby the projecting edge of a planar element is insertable and slidable in the notch of another planar element, at least one portion of the projecting edge and at least one portion of the notch more preferably belonging to the lower plate.

Always according to the invention, said first mechanical coupling means may comprise at least one screw.

Still according to the invention, the upper plate of at least one planar element may have a larger surface than the lower plate, a lower surface of the upper plate having a hollowed seat capable to house the lower plate, said first mechanical coupling means comprising a screw.

Furthermore according to the invention, said second mechanical coupling means may comprise at least one screw removably attachable to the planar element through a respective slot of the slab, said at least one screw further preferably belonging to said first mechanical coupling means.

Always according to the invention, said first material may be selected from the group comprising polytetrafluoroethylene (PTFE), silicone and polymethylmethacrylate (PMMA), the upper plate preferably having thickness ranging from 8 mm to 40 mm.

Still according to the invention, said second material may be metal, preferably selected from the group comprising stainless steel and titanium, the lower plate more preferably having thickness ranging from 3 mm to 15 mm.

Furthermore according to the invention, the device may further comprise a frame attached to the slab, capable to be connected with adjustable spatial orientation, through third mechanical coupling means for coupling to an operating table, said third mechanical coupling means preferably comprising a first joint for connecting the frame to a first arm which is in turn connected, through a second joint, to a second arm capable to be connected to an operating table.

It is still specific subject matter of this invention an automatic method for computing distribution of dose radiated by a IORT machine through a device for shaping an electron beam as previously described, comprising the following steps:

acquiring arrangement of said at least one planar element,
acquiring energy of electron beam generated by the IORT machine,
determining a three-dimensional dose distribution after the device for shaping the electron beam corresponding to the arrangement of said at least one planar element, on the basis of simulated data, preferably according to a Monte Carlo simulation, of the three-dimensional dose distribution.

The device according to the invention is capable to spatially shape the electron beam exactly on the target. This allows, on the one hand, to treat through IORT all the neoplasias intrinsically having a shape not reducible to the circular symmetry (e.g., the sarcomas), and, on the other hand, to improve the possibility of defining the so-called Planning Target Volume (i.e. the volume to radiate that is wider than the clinical volume containing the tumor bed for taking account of the movements of tissues and organs) significantly avoiding the involvement of healthy tissues and organs.

Moreover the device according to the invention permits to execute radiation joining fields. By way of example, in the preferred embodiment of the device, that shapes the electron beam so that the cross section thereof is a rectangle with adjustable size, it is possible to carry out subsequent radiations by joining the radiated rectangular areas.

Still, the machine for IORT provided with the device according to the invention comprises processing means preferably capable to execute a method for computing the dose distribution obtained through the same device according to the invention.

The present invention will be now described, by way of illustration and not by way of limitation, according to its preferred embodiments, by particularly referring to the Figures of the enclosed drawings, in which:

FIG. 1 shows a top perspective view of a preferred embodiment of the device for shaping an electron beam according to the invention in a first configuration, along with a distal element of an applicator;

FIG. 2 shows a left side view of the device of FIG. 1;

FIG. 3 shows a front view of the device of FIG. 1;

FIG. 4 shows a partial top plan view of the device of FIG. 1;

FIG. 7 shows a top perspective view (FIG. 7a), a bottom perspective view (FIG. 7b), a top plan view (FIG. 7c), a front view (FIG. 7d), a right side view (FIG. 7e), and a rear view (FIG. 7f) of a planar element of the device of FIG. 1;

Figure 5:
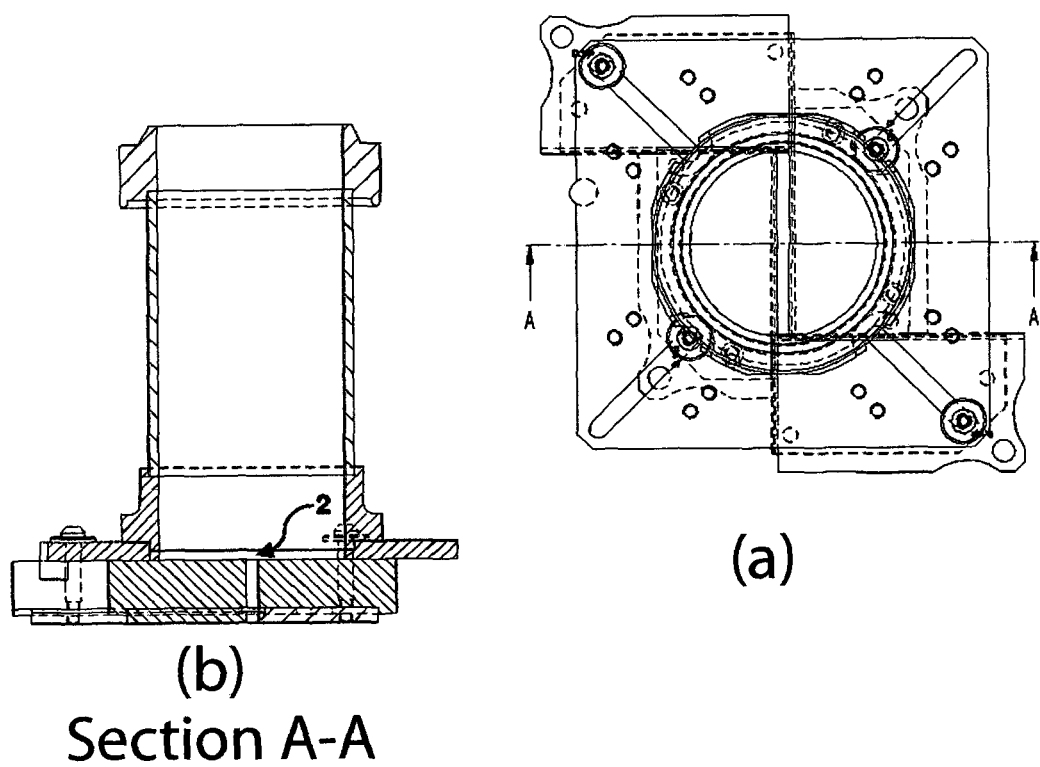
FIG. 5 shows a top plan view (FIG. 5a) and a cross section view along AA line of FIG. 5a (FIG. 5b) of a portion of the device of FIG. 1.
Figure 8:
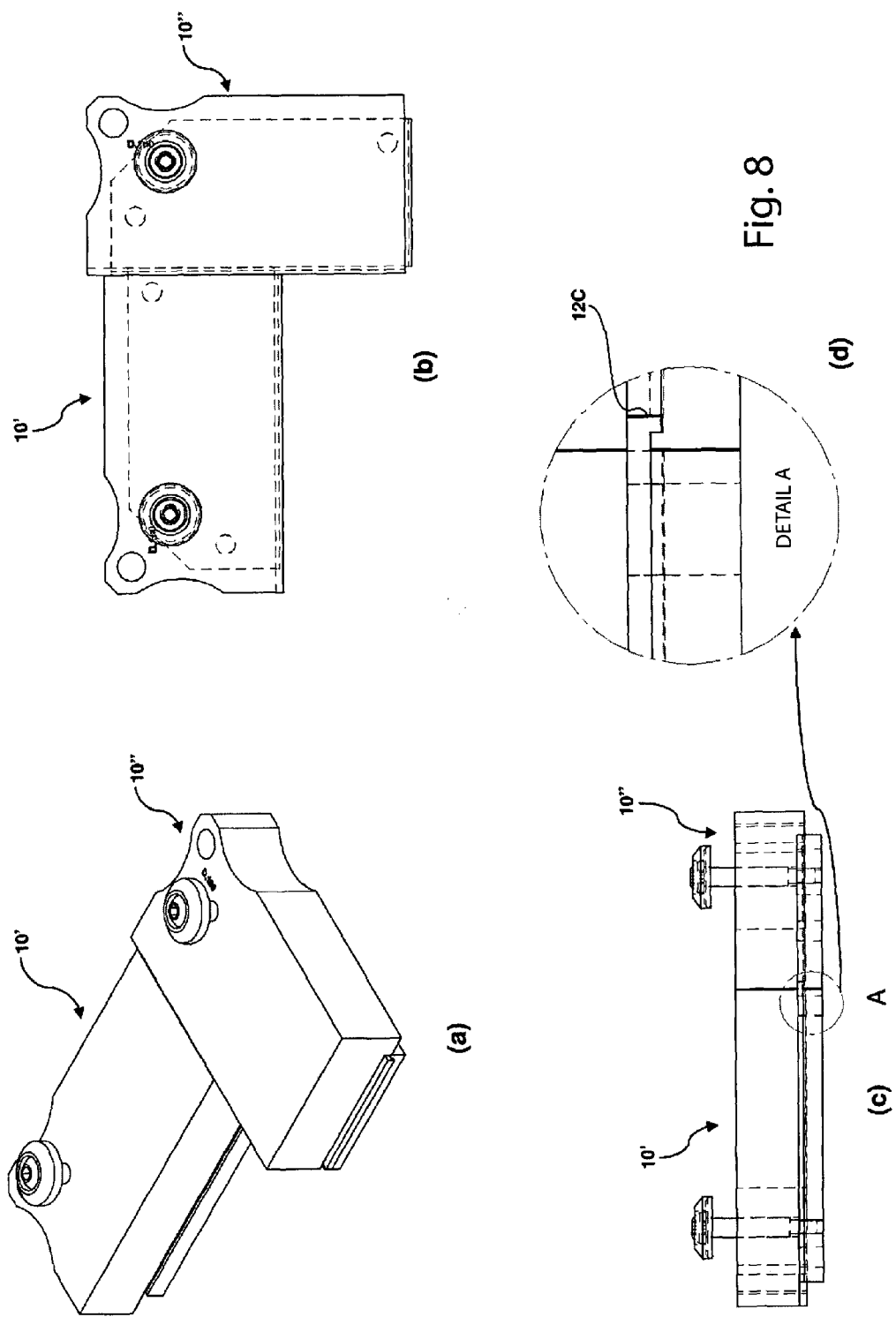
Figure 9:
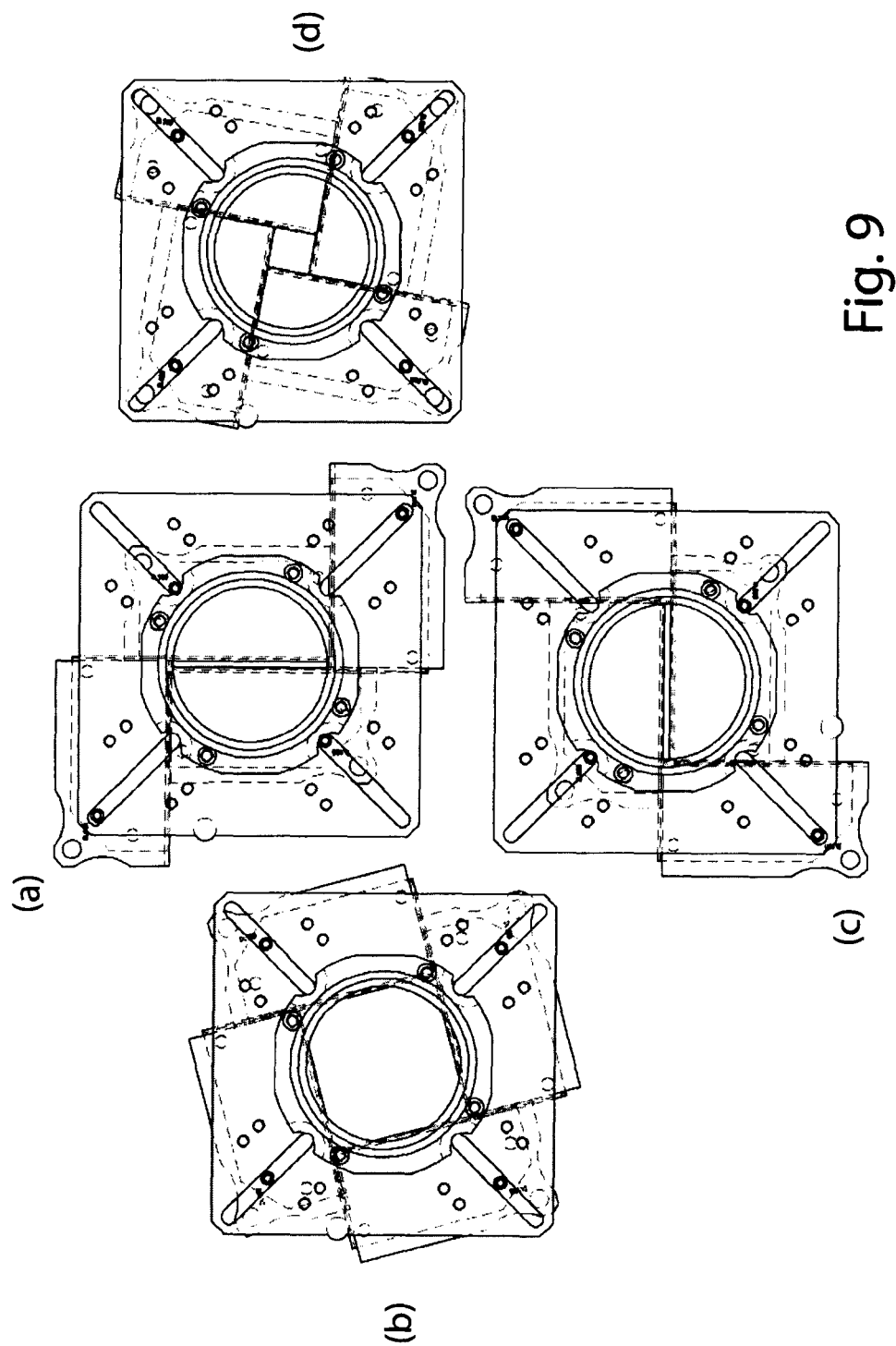

FIG. 8 shows a top perspective view (FIG. 8a), a top plan view (FIG. 8b), a front view (FIG. 8c), and an enlargement of a particular of the front view (FIG. 8d) of two adjacent planar elements of the device of FIG. 1; and FIG. 9 shows a top plan view in the first configuration (FIG. 9a), in a third configuration (FIG. 9b), in a fourth configuration (FIG. 9c), and in a fifth configuration (FIG. 9d) of the portion of FIG. 5.

In the following description same reference numbers will be used for indicating alike elements in the Figures.

In particular, dimensions shown in the Figures are by way of example and have not to be intended as limiting the scope of protection of the present invention, unless expressly indicated to the contrary.

In the following of the description reference will be made to some preferred embodiments of the device according to the invention having four identical planar elements, each one formed by two overlapping plates made of different materials, wherein the planar elements are pairwise adjacent and mutually orthogonally slide through the interaction of a slider and of a corresponding guide so as to define a rectangular aperture. However, it should be noted that the device according to the invention may comprise any number of planar elements, even with a single planar element adjustably coupled to the slab, in the case where they are at least two planar elements these may be adjacent or not, in the case where they are at least three the planar elements may be pairwise adjacent and mutually orientated according to respective angles, which angles may possibly be also variable and/or adjustable, and/or that the planar elements may be different from each other, and/or that each planar element may comprise a single plate of a single material or a number of plates larger than two, possibly also made of the same material, and/or that the planar elements adjacent may mutually slide through different mechanical guide and slide means, and/or that the planar elements may define an aperture with shape different from a rectangle, still remaining within the scope of protection of the present invention as defined by the attached claims.

With reference to FIGS. 1-5, it may be observed that the preferred embodiment of the device according to the invention comprises a slab 1, with substantially square shape, centrally provided with a circular hole 2 (shown in FIGS. 4 and 5) with diameter equal to the diameter of the circular applicator used with the IORT machine; in particular, in the Figures the distal element 3 of a circular applicator used in the LIAC is shown. It should be noted that the diameter of the circular hole 2 and of the circular applicator may be also not equal, and that also the shape of the hole 2 may be not corresponding to that of the applicator duct.

The preferred embodiment of the device according to the invention further comprises four planar elements 10, identical to each other, arranged so as to be pairwise adjacent, which, as it will be described in greater detail below, are capable to mutually orthogonally slide so as to define a rectangular aperture 20 and each one of which is formed by two overlapping plates made of different materials: an upper plate 11 preferably of polytetrafluoroethylene (PTFE, also known with the trade name Teflon®) and a lower plate 12 preferably of stainless steel. The two plates 11 and 12 of each planar element 10 are mutually removably attached through a respective screw 13, that further ensures the removable attachment of each planar element 10 to the slab 1 in a variable position with continuity as a function of the attachment position of the screw 13 along a respective slot 14 of the slab 1.

Figure 6:
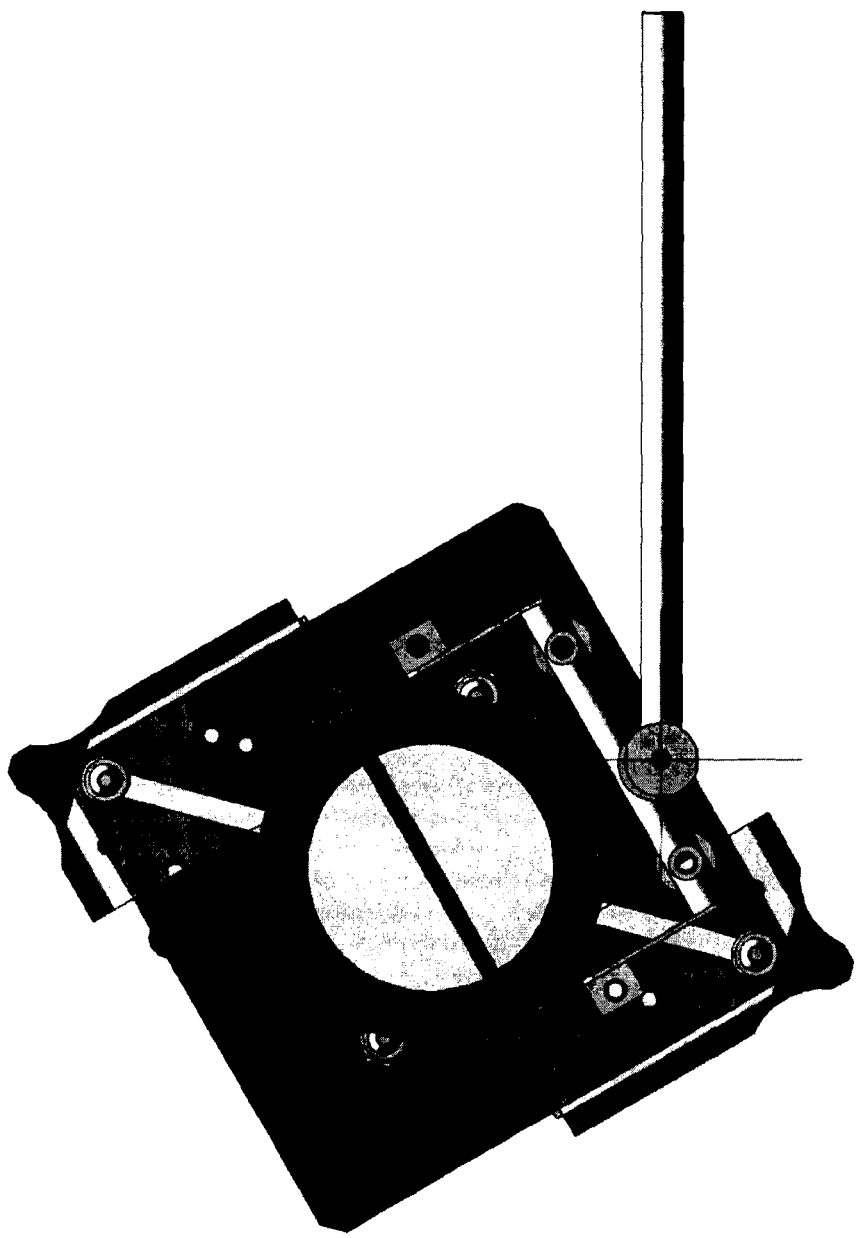
FIG. 6 shows a partial top plan view, wherein also hidden components are visible, of the device of FIG. 1 in a second configuration.

Preferably, the device further comprises a frame 4 (not shown in FIG. 5) attached in four points to the slab 1, connected, through a first joint 5, to a horizontal arm 6 which is in turn connected, through a second joint 7, to an arm 8 supporting the device. In particular, the supporting arm 8 is provided, at the lower end, with a conventional vice attachment 9 for attaching to a universal mechanical guide of an operating table (not shown in the Figures), allowing the attachment of the device according to the invention to the operating table on which the patient to be subjected to IORT lies. Through the frame 4, the arms 6 and 8 and the joints 5 and 7, the device for shaping the electron beam may be moved in space: the second joint 7 allows both to move the horizontal arm 6 along the supporting arm 8, thus adjusting the height of the device with respect to the operating table, and to make a pitch movement of the horizontal arm 6, and consequently of the device, with respect to the supporting arm 8; the first joint 5 allows both to make a roll movement of the frame 4 and consequently of the device, with respect to the horizontal arm 6, and to modify the angle onto the plane of the slab 1 between frame 4 and horizontal arm 6, as shown by way of example in FIG. 6.

With reference to FIG. 7, it may be observed that each one of the planar elements 10 is formed by an upper plate 11, preferably of polytetrafluoroethylene (PTFE) and a lower plate 12, preferably of stainless steel, the upper plate 11 having a larger surface than the lower plate 12. The upper plate 11 and the lower plate 12 have a main short side, respectively 11A and 12A, and a main long side, respectively 11B and 12B. The lower surface of the upper plate 11 has a hollowed seat wherein the lower plate 12 may be housed, so that the respective main short sides 11A and 12A and the respective main long sides 11B and 12B are aligned; moreover, such hollowed seat avoids that, once the screw 13 has been attached, the plates 11 and 12 move with respect to one another, also by mutual rotation. Other embodiments of the device for shaping the electron beam according to the invention may have mechanical means for attaching the plates 11 and 12 that is different from the screw 13 and the hollowed seat on the lower surface of the upper plate 11.

The main short side 12A of the lower plate 12 has a projecting edge 12C with L-shaped section towards the lower surface of the lower plate 12. The main long side 12B of the lower plate 12 has a notch 12D with L-shaped section with shape and size corresponding to the ones of the projecting edge 12C of the main short side 12A; in this regard, the main long side 11B of the upper plate 11 inferiorly has a notch 11D shaped with rectangular section with size at least sufficient to house the projecting edge 12C of another planar element 10.

As shown in FIG. 8, two adjacent planar elements 10' and 10" are arranged orthogonally to one another, i.e. with the main short side of the upper and lower plates of the first one facing the main long side of the upper and lower plates of the second one. The projecting edge 12C' of the first planar element 10' is inserted, through sliding, in the notch 12D" of the second planar element 10"; in this way, the projecting edge 12C' is engaged and slidable within the notch 12D", wherein it is kept by the overlying surface of the notch of the upper plate 11. In other words the projecting edges 12C and the notches 12D of the planar elements 10 constitute mechanical guide and slide means allowing the four planar elements 10 to be attached to each other in an adjustable manner; in particular, the projecting edges 12C operate as sliders and the notches 12D operate as guides. Thanks to the possibility to make the planar elements 10 slide along the respective slots 14 and to make the same planar elements 10 rotate with respect to the respective slots 14, this allows to shape the electron beam (i.e. the radiation field) in rectangular fields of any size inscribed in a surface contained within the circular field defined by the circular applicator, as shown by way of example in FIG. 9, eliminating any gap among the planar elements. In this regard, possible rotations of the planar elements 10, and consequently of the rectangular fields defined by these, with respect to the area to radiate may be compensated by rotating the frame 4 with respect to the horizontal arm 6 through the first joint 5, as shown by way of example in FIG. 6.

Other materials may be used instead of PTFE for the upper plate 11 and of stainless steel for the lower plate 12. Criteria for selecting the plate materials for the preferred embodiment of the device according to the invention provide that: the material of the upper plate 11 is a biocompatible sterilisable material with low atomic number (Z) so as to interact with the electron beam generated by the IORT machine in a similar way to water, i.e. by braking it without producing many X-rays (by way of example and not by way of limitation, other materials usable for the upper plate 11 besides PTFE are silicone and PMMA); the material of the lower plate 12 is a biocompatible sterilisable material ensuring mechanical robustness to the planar element 10, and with high Z so as to attenuate the few X-rays produced by the upper plate 11 (by way of example and not by way of limitation, another material usable for the upper plate 12 besides stainless steel is titanium).

With regard to thicknesses of the upper and lower plates, they depend on the used material, on the energy of the electron beam to stop, and on the desired efficiency of beam stopping. In the case where the upper plate 11 is of PTFE and the lower plate 12 is of stainless steel, in order to obtain a mean residual dose at surface under the planar element 10 lower than 3% of the maximum dose ($D_{MAX}$), it follows that, for a beam energy ranging from 4 MeV to 16 MeV, the thickness of the upper plate 11 preferably ranges from 8 mm to 40 mm and the thickness of the lower plate 12 preferably ranges from 3 mm to 15 mm; more in particular: in the case where the energy is 4 Mev, the upper plate 11 has preferably thickness of 8 mm and the lower plate 12 of stainless steel has preferably thickness of 3 mm; in the case where the energy is 12 Mev, the upper plate 11 has preferably thickness of 26 mm and the lower plate 12 of stainless steel has preferably thickness of 8 mm; in the case where the energy is 16 Mev, the upper plate 11 has preferably thickness of 40 mm and the lower plate 12 of stainless steel has preferably thickness of 15 mm.

In the following some criteria for selecting the materials of the upper and lower plates and the related thicknesses are described in greater detail.

One of the requirements for determining the materials is obtaining a high attenuation of the electron beam outside the rectangular field defined by the planar elements, with a mean residual dose at surface under the planar elements lower than 3% of the $D_{MAX}$ with the beam of maximum energy available from the IORT machine. The best solution for braking the electron beam, keeping the photon production rate due to Bremsstrahlung (i.e. braking radiation) as low as possible and minimising the necessary thickness, is the use of two different materials: the first one with low Z, the second one with higher density (i.e. with high Z). Other requirements are those of sterilisability and biocompatibility of all the device components, in particular the planar elements 10.

The study for dimensioning the thicknesses may be carried out, as a first approximation, with the CSDA (Continuous Slowing Down Approximation) schematisation for the interaction between electron beam and matter. This schematisation provides for both the average range of the electrons of a certain energy and an estimation of the photon production due to Bremsstrahlung; data related to all the elements and to numerous compounds of common use in radiotherapy are available on-line, e.g. at the site http://physics.nist.gov/PhysRefData/Star/Text/ESTAR.html.

The CSDA range (RCSDA) is a good approximation of the length of the average path run by a charged particle in a medium, evaluated as if it slowed down in a continuous way to a stop (Continuous Slowing Down Approximation). In this approximation, the fraction of lost energy at each point along the particle track is assumed as equal to its total stopping power. Fluctuations of lost energy are neglected. The RCSDA is obtained from integration of the reciprocal of the total stopping power with respect to the energy. The total stopping power for the electrons is the sum of the collisional stopping power and of the radiative stopping power. The latter is the fraction of lost energy per unit of run length due to collisions with atoms and atom electrons wherein photons are emitted due to Bremsstrahlung. For the electrons it is important to evaluate the average fraction of initial kinetic energy of an electron that is converted in photons due to Bremsstrahlung. These quantities are the basis for the computations necessary to ensure safety for the patient and environmental radiation protection.

The current accelerated within the linear accelerator (linac) of the IORT machine may be schematised as a beam with cylindrical symmetry with super-Gaussian profile until the impact with the linac output window. Hence, using the CSDA approximation, the dose deposition and the radiation production due to Bremsstrahlung along the beam path until the impact with the device for shaping the beam according to the invention may be computed. Data necessary to computation, related to the radiation-matter interaction, are available on the Internet at the address http://physics.nist.gov/PhysRefData/Star/Text/ESTAR.html.

The analysis may be made for all the energies available from a IORT machine, in particular a LIAC (i.e.: 4, 6, 8, 10 and 12 MeV), in which, thanks to the absence of bending magnets and to the manufacture with materials with low Z, scattered radiation is kept at very low levels. It is possible to use a modelling for the direct computation of the dose by using the RCSDA approximation. The dose deposited in water, for instance, may be expressed as:

$$D_W = \int_0^{T_{MAX}} \Phi_{T'} \left[ \left( \frac{dT}{\rho dx} \right)_{c,w} \right]_{T'} dT'$$

where $D_W$ represents the dose deposited in a thickness dx of water ($\rho$ is water density) by an electron beam with kinetic energy from 0 to $T_{MAX}$ with fluence $\Phi$. The fluence is computable as:

$$\Phi_{pulse} = \frac{i_{beam} \cdot t_{pulse}}{S_{Appl}}$$

that is as the product of the current of the beam $I_{beam}$ by the time of a pulse $t_{pulse}$ divided by the section of the applicator $S_{Appl}$. Considering the thickness t computed in CSDA approximation $$t = R_{CSDA}(T_0),$$

it is possible to compute the dose deposited in the thickness t in the medium of density $\rho$. In this way it is possible to speculate configurations of the device according to the invention with at least two materials with thicknesses such as to ensure an efficient shielding for healthy tissues and with low X-ray production due to Bremsstrahlung.

For evaluating the Bremsstrahlung produced by the crossing of the material, it is possible to carry out a weighted average of the radiation yield upon variation of the point of crossed material; hence, the attenuation due to the thickness of the lower plate is evaluated. For evaluating the energy of the beam incident on the planar elements 10 of the device according to the invention, measurements of PDD (Percentage Depth Dose) at field centre are used. This choice, useful for saving the computation time, is strongly conservative: the planar elements will not be invested by the beam at field centre (this would imply a configuration of the device according to the invention completely closed shielding the whole electron beam) but in more peripheral zones where in the spectrum of the beam the components scattered by the material (preferably PMMA) of the cylindrical applicator predominate and thus the average energy is lower.

Bay way of example, for PTFE and iron (of the stainless steel) the tables related to the stopping power, the radiation yield and RCSDA upon variation of the electron beam energy may be obtained from the aforementioned web site ESTAR on the basis of which it is possible to compute in CSDA approximation the attenuation of the beam by the planar elements 10 of the device according to the invention. On the basis of the PDD, R50 (depth at which the dose reduces down to 50% of the maximum value) of the electron beam of 12 MeV is 4.7 cm; thus the beam has an average energy $E_{ave}$ of 10.98 MeV $$E_{ave} = 2.33 \text{ [MeV} \cdot \text{cm}^{-1}] \cdot \text{R50 [cm]}).$$

Table I shows the reduction of the electron beam as a function of the crossing of the upper plate 11 of PTFE: besides the average energy of the electron beam (E beam avg. Energy [MeV]), the energy fraction transformed in X-rays due to Bremsstrahlung (radiation yield) and the average energy of the generated X radiation (X ray avg. energy [MeV]) upon variation of the thickness of crossed PTFE are shown.

TABLE I

| crossed PTFE thickness (cm) | E beam avg. Energy (MeV) | radiation yield | X ray avg. energy (MeV) |
| --- | --- | --- | --- |
| 0 | 10.76 MeV | 0.050 | 2.7 MeV |
| 0.2 | 10.01 MeV | 0.050 | 2.5 MeV |
| 0.4 | 9.26 MeV | 0.050 | 2.3 MeV |
| 0.6 | 8.50 MeV | 0.045 | 2.1 MeV |
| 0.8 | 7.75 MeV | 0.035 | 1.9 MeV |

TABLE I-continued

| crossed PTFE thickness (cm) | E beam avg. Energy (MeV) | radiation yield | X ray avg. energy (MeV) |
|---|---|---|---|
| 1 | 7.00 MeV | 0.030 | 1.7 MeV |
| 1.2 | 6.25 MeV | 0.030 | 1.6 MeV |
| 1.4 | 5.49 MeV | 0.025 | 1.4 MeV |
| 1.6 | 4.74 MeV | 0.020 | 1.2 MeV |
| 1.8 | 3.99 MeV | 0.020 | 1.0 MeV |
| 2 | 3.23 MeV | 0.015 | 0.8 MeV |
| 2.2 | 2.48 MeV | 0.010 | 0.6 MeV |
| 2.4 | 1.73 MeV | 0.010 | 0.4 MeV |
| 2.6 | 1.16 MeV | 0.010 | 0.3 MeV |

When impacting the lower plate 12 of steel the electron beam has hence an average energy of 1.16 MeV. The CSDA range for such beam is lower than 0.1 cm and, hence, no electron comes out from the steel plate. The thickness of the lower plate 12 of steel is selected as equal to 8 mm for ensuring a significant attenuation of the X-rays produced by the upper plate 11 and for giving robustness to the planar element 10. The energy fraction converted into X-rays is about 2.9% with an average energy of about 1.5 MeV. In literature it is known that the radiation lobe has a cardioid shape strongly peaked towards the beam direction. The attenuation of 0.8 mm of steel is computable as $e^{-\mu \cdot p \cdot \delta x}$ where

| ρ | 7.87 g/cm$^3$ |
|---|---|
| μ @ 1.5 MeV | 5.35E−02 cm$^2$/g | and δx is the thickness of crossed material, i.e. 0.8 cm. The attenuation is equal to about 30%. Hence the energy fraction going beyond the steel barrier is about 2% of the energy conveyed by the electron beam. It is possible to provide an approximated estimation of the dose deposited by the X-rays considering that (conservatively) they deposit 90% of energy in 25 cm of water; this implies that, since the electrons deposit all their energy in 6.5 cm of water, the dose deposited at $D_{MAX}$ by the photons under the planar elements 10 is absolutely lower than 1% with respect to the dose at filed centre at $D_{max}$. Consequently, the requirement that the mean residual dose at surface under the planar elements is lower than 3% of the $D_{MAX}$ with the beam of maximum energy available from the IORT machine is fully satisfied.

The materials used in the preferred embodiment of the device according to the invention, i.e. PTFE and stainless steel, also ensure biocompatibility and enable to use the autoclave sterilisation at 134° C.

The inventors have further developed a method, followed by a software executed by processing means of the IORT machine, for automatically computing the dose distribution in any configuration of the planar elements 10, i.e. for any rectangular aperture defined by the selected arrangement of the planar elements 10.

Monte Carlo (MC) codes allow to simulate the behaviour of the electron beam in complex geometries. In a design phase the MC may be a useful tool for reproducing particularly critical measurements due to the intrinsic instrumental limits and to the complex experimental procedures. The code used by the inventors is EGSnrcMP/BEAMnrcMP, distributed by Ionizing Radiation Standards Group—National Research Council of Canada, on the Internet at the address http://www.irs.inms.nrc.ca/BEAM/user_manuals/DISTRIBUTION.html. BEAMnrcMP is a system of Monte Carlo simulation that has been conceived for modelling sources for radiotherapy and that is based on the EGSnrcMP code that simulates the conveyance of electrons and photons. The used version puts at the user's disposal a graphical interface (GUI) enabling to construct the geometry of the conveyance line of the beam (i.e. the cylindrical applicator) and to set the conveyance parameters and the options for the cross sections in a faster way.

Measurements of spatial dose distribution have been made: curves of depth dose deposition (PDD) and profiles made at different depths so as to obtain isodose curves. Measurements have been made on the whole interested volume so as to determine the exact three-dimension distribution of the dose deposition (i.e. on the target placed after the device for shaping the electron beam according to the invention) obtained in the different conditions of shaping the electron beam (i.e. of configuration of the planar elements 10). In particular, these measurements have been made with 3D powered water phantom (e.g. the RFA 300 phantom available from IBA Dosimetry GmbH) and with beam analyser (e.g. MP3-XS Therapy beam analyser available from PTW Freiburg GmbH). In particular, there have been used as sensors the diodes for electrons of IBA Dosimetry GmbH and the pinpoint isotropic cylindrical chamber of PTW, making specific solid phantoms with suitable housings for the sensors.

The result of the Monte Carlo simulation has been that of obtaining an accurate reproduction of the three-dimensional dose distribution and of computing the multiplicative factors for each configuration of the device for shaping the beam with respect to the reference one (that has the field completely open). The simulation allows to reproduce any desired configuration and to associate with it an output factor. The phantom measurement has allowed a sampled verification and possibly a feedback for modifying the simulation.

Through the MC simulation and the made measurement, it has been possible to make deterministic methods (algorithms), implementable by means of the software executed by the processing means of the IORT machine, for the automatic computation of the distribution of dose deposited by the shaped beam that enables to determine in real time the dose delivered to the clinical volume. In particular, it is possible that the size of the aperture defined by the planar elements 10 is acquired, digitised and transmitted manually by an operator or even automatically (through suitable sensors) to the processing means of the IORT machine that will then use it in the automatic computation of the dose distribution.

As stated above, the results obtained with the Monte Carlo simulation have been inserted in the automatic method of computation, whereby, once the size of the radiation field and the energy of the electron beam generated by the IORT machine have been acquired, the method computes the dose distribution through the deterministic algorithms determined with the simulation and the measurements. This allows to determine in real time the dosimetric characterisation as a function of the geometric arrangement of the device according to the invention so that it is possible to provide data for setting the IORT machine, e.g. the LIAC, during treatment of a patient with shaped beam.

Preferably, the IORT machine is further provided with a centring system, comprising a field light and a laser pointer, for enabling localisation of the target and ensuring the efficiency of the IORT. The field light simulates the propagation of the beam along the cylindrical applicator and the interaction with the device for shaping the beam according to the invention, so as to exactly illuminate the target; the laser pointer is used for exactly determining the direction of the beam and its symmetry axis. Both the field light and the laser pointer are advantageously provided with a mechanical interface ensuring the applicability to the radiating head of the IORT machine and the ease and rapidity of use.

The procedure that is followed in using the device for shaping the electron beam according to the invention may be the following:
- the surgeon chooses, along with the radiotherapist, the area to treat;
- before mounting it on the cylindrical applicator, the device for shaping the electron beam is prepared, by adjusting the planar elements 10, according to the desired shape and size of the radiation field, also thanks to the aid of millimeter scales present on the planar elements 10;
- the device for shaping the electron beam is then placed in correspondence with the surgical incision through the attachment of the supporting arm 8 to the operating table and the adjustment of the joints 5 and 7;
- finally, the procedure of hard docking of the cylindrical applicator with the device for shaping the electron beam is executed.

Afterwards, the dedicated software automatically provides for computing the dose distribution in the chosen configuration.

Other embodiments of the device for shaping the electron beam according to the invention may further provide that it is removably attachable to the distal end of the applicator.

Further embodiments of the device for shaping the electron beam according to the invention may further provide that it is mounted before a distal element of the cylindrical applicator, e.g. of length equal to 5 cm, that is then inserted into the surgical incision; the field will be equally formed and the software is capable to compute the enlargement of the electron beam after the shaping device.

The preferred embodiments have been above described and some modifications of this invention have been suggested, but it should be understood that those skilled in the art can make variations and changes, without so departing from the related scope of protection, as defined by the following claims.

The invention claimed is:

1. Electron beam shaping device suitable for a machine for intraoperative radiation therapy (IORT—Intra Operative Radiation Therapy), said machine comprising a mobile unit, provided with a linear accelerator having an electrons radiating head, and an operating control rack, which are wired connected to each other, said shaping device including a circular applicator, comprising a cylindrical tube and having a duct through which the electron beam is transmitted, which is rigidly attached to said radiating head and which includes a proximal element, that is attached to said radiating head, and a distal element (3), that is placed in contact with the area to radiate and that is attached to said proximal element, the shaping device being characterised in that it comprises:
- a slab (1), which is removably attached to said distal element (3) and which is provided with a hole (2) corresponding to the duct of the circular applicator,
- at least two planar elements (10), whereby each planar element (10) comprises two overlapping plates (11, 12) which are attached to each other through first mechanical coupling means (13) and whereby each planar element (10) is attached to said slab (1) in a variable position with continuity as a function of the attachment position of said first mechanical coupling means (13) and of second mechanical coupling means (14),
said at least two planar elements (10) being reciprocally arranged so as to be adjacent to each other and each planar element (10) sliding with respect to another adjacent planar element (10) through mechanical guide and slide means (12C, 12D), whereby the reciprocal arrangement of said at least two planar elements (10) is adjustable so as to define an aperture (20) of lower area than that of the section of the duct of said circular applicator,
said two overlapping plates (11, 12) being made of different materials, so that a first plate (11) is made of a first sterilisable material with a first atomic number and a second plate (12) is made of a second sterilisable material with a second atomic number larger than the first atomic number, whereby the second plate (12) attenuates X-rays produced by the first plate (11).

2. Device according to claim 1, characterised in that said mechanical guide and slide means (12C, 12D) comprises at least one slider (12C) and at least one corresponding guide (12D).

3. Device according to claim 1, characterised in that said planar elements (10) are four, each planar element (10) having a first side (11A, 12A) provided with a projecting edge (12C) with an L-shaped section,—and a second side (11B, 12B) provided with a notch (11D, 12D) with an L-shaped section, of shape and size corresponding to the ones of the projecting edge (12C), whereby the projecting edge (12C') of a planar element (10') is insertable and slidable in the notch (12D") of another planar element (10").

4. Device according to claim 1, characterised in that said first mechanical coupling means (13) comprises at least one screw (13).

5. Device according to claim 1, characterised in that the first plate (11) of at least one planar element (10) has a larger surface than the second plate (12), a lower surface of the first plate (11) having a hollowed seat that houses the second plate (12), said first mechanical coupling means (13) comprising a screw (13).

6. Device according to claim 1, characterised in that said second mechanical coupling means (13, 14) comprises at least one screw (13) which is attached to the planar element (10) through a respective slot (14) of the slab (1).

7. Device according to claim 1, characterised in that said first sterilisable material is selected from the group comprising polytetrafluoroethylene (PTFE), silicone and polymethylmethacrylate (PMMA), the first plate (11) having thickness ranging from 8 mm to 40 mm.

8. Device according to claim 1, characterised in that said second sterilisable material is a metal selected from the group comprising stainless steel and titanium, said second plate (12) having a thickness ranging from 3 mm to 15 mm.

9. Device according to claim 1, characterised in that it further comprises a frame (4) attached to the slab (1) and connected with adjustable spatial orientation, through third mechanical coupling means (5, 6, 7, 8, 9) for coupling to an operating table, said third mechanical coupling means comprising a first joint (5) for connecting the frame (4) to a first arm (6) which is in turn connected, through a second joint (7), to a second arm (8) connected to the operating table.

10. Automatic method for computing distribution of dose radiated by a IORT machine through a device for shaping an electron beam according to claim 1, comprising the following steps:
- measuring data related to said aperture (20) due to the reciprocal arrangement of said at least two planar elements (10),
- measuring the energy of the electron beam generated by the IORT machine, determining a three-dimensional dose distribution after the device for shaping the electron beam corresponding to the reciprocal arrangement of said at least two planar elements (10), on the basis of simulated data, preferably according to a Monte Carlo simulation, of the three-dimensional dose distribution.

* * * * *